(12) United States Patent
Elder

(10) Patent No.: US 9,903,879 B2
(45) Date of Patent: Feb. 27, 2018

(54) METHOD TO ALLOW FOR LINKING TEMPORAL RECORD WITH PHYSIOLOGICAL MEASUREMENT IN BUTTONLESS PHYSIOLOGICAL METERS

(71) Applicant: LifeScan Scotland Limited, Inverness-shire (GB)

(72) Inventor: David Elder, Inverness (GB)

(73) Assignee: LifeScan Scotland Limited, Inverness (GB)

(*) Notice: Subject to any disclaimer, the term of this patent is extended or adjusted under 35 U.S.C. 154(b) by 300 days.

(21) Appl. No.: 13/827,296

(22) Filed: Mar. 14, 2013

(65) Prior Publication Data

US 2014/0269216 A1 Sep. 18, 2014

(51) Int. Cl.
*G01N 33/48* (2006.01)
*G01N 35/00* (2006.01)
*C12Q 1/00* (2006.01)
*G01N 33/487* (2006.01)
*G06G 7/58* (2006.01)

(52) U.S. Cl.
CPC ....... *G01N 35/00029* (2013.01); *C12Q 1/006* (2013.01); *G01N 33/48792* (2013.01); *G01N 2035/00108* (2013.01)

(58) Field of Classification Search
None
See application file for complete search history.

(56) References Cited

U.S. PATENT DOCUMENTS

| | | | |
|---|---|---|---|
| 5,410,474 A | 4/1995 | Fox | |
| 5,897,493 A * | 4/1999 | Brown | 600/300 |
| 6,797,150 B2 | 9/2004 | Kermani et al. | |
| 6,856,125 B2 | 2/2005 | Kermani | |
| 6,872,298 B2 | 3/2005 | Kermani | |
| 7,195,704 B2 | 3/2007 | Kermani et al. | |
| 7,749,371 B2 | 7/2010 | Guo et al. | |

* cited by examiner

*Primary Examiner* — Eric S Dejong

(57) ABSTRACT

Described are methods and systems to allow the use of a very simple physiological meter without a user input interface (i.e., buttonless) while maintaining the ability to store time linked measurement records for retrospective or prospective analysis of the measured physiological measurements.

10 Claims, 3 Drawing Sheets

METHOD TO ALLOW FOR LINKING TEMPORAL RECORD WITH PHYSIOLOGICAL MEASUREMENT IN BUTTONLESS PHYSIOLOGICAL METERS

BACKGROUND

Physiological measurements can be performed with a wide variety of known physiological measurement devices. For example, body temperature, cardiac rhythm, blood pressure, oxygen saturation in blood, electrocardiography, EEG, pulse, skin conductance, total hemoglobin, carboxyhemoglobin, methemoglobin, perfusion index and the like can be monitored with small handheld instrument or meter. Similarly, physiological measurements can be made of analytes (glucose, ketone, cholesterol and the like) present in physiological fluids, e.g. blood, blood derived products, or other fluids in biological systems. Physiological detection find use in a variety of applications, including clinical laboratory testing, home testing, hospitals, clinical, etc., where the results of such testing play a prominent role in diagnosis and management in a variety of disease conditions.

One area that applicants have concentrated is the physiological monitoring of persons with diabetes. In such person, glucose monitoring is one technique to ensure normal glycemic state of such person. The accuracy of such monitoring can significantly affect the health and ultimately the quality of life of the person with diabetes. Generally, a diabetic patient measures blood glucose levels several times a day to monitor and control blood sugar levels. Failure to test blood glucose levels accurately and on a regular basis can result in serious diabetes-related complications, including cardiovascular disease, kidney disease, nerve damage and blindness. There are a number of electronic devices currently available which enable an individual to test the glucose level in a small sample of blood. One such glucose meter is the OneTouch® Profile™ glucose meter, a product which is manufactured by LifeScan.

There currently exist a number of portable electronic devices that can measure physiological parameter(s) (e.g., body temperature, cardiac rhythm, blood pressure, oxygen saturation in blood, electrocardiography, EEG, pulse, skin conductance, total hemoglobin, carboxyhemoglobin, methemoglobin, perfusion index, glucose levels, ketone, cholesterol and the like) in an individual and store the measurements for recalling or uploading to another computer or remote processor for analysis. These devices are provided with user input interfaces such as buttons and capacitive touchscreen to allow the user to manipulate information or configure parameters for the meter.

It has been proposed by others in the art to utilize a buttonless physiological meter, as shown and described in U.S. Pat. No. 5,410,474, which is incorporated by reference herein. From the standpoint of the users, a meter without any button or user input interface is very attractive due to its operational simplicity. Nevertheless, such systems are susceptible to various modes of inefficiency or error.

SUMMARY OF THE DISCLOSURE

Applicants have recognized that a person managing a chronic disease (e.g., diabetes, asthma, high blood pressure and the like) with a buttonless physiological monitor described earlier faces the problem of accessing that person's prior physiological measurements quickly and intuitively in the absence of any user input interface (buttons, touchscreen, or voice-command and the like). For the manufacturer of such meter, there is a lower cost of manufacturing because the deletion of a user input interface (e.g., buttons, touch screen or non-contact touchscreen). However, a meter without a user input interface does not allow for manipulation of the temporal parameters (e.g., time, date or both time and date). Consequently, any stored physiological measurement will not have a time record or time-stamp to indicate when the physiological measurement was taken. This would render the physiological measurement records virtually worthless without the measurements being linked to the appropriate temporal parameters.

In one aspect, a method of linking a time record for each physiological measurement in a physiological measurement system is provided. The system has a physiological meter with a microprocessor linked to a clock, memory, display and configured such that the meter is without any user input interface for a user to set temporal parameters including time for the physiological meter. The method can be achieved by: determining whether the clock has been reset, and if true, evaluating whether a clock reset flag has been set; if the evaluating step is false then setting a clock reset flag and setting the clock to its initial factory parameters, otherwise if the evaluating step is true then disqualifying any physiological measurement record having a delta-time flag associated with the record; if the determining step is false then querying as to whether a physiological measurement has been made; if the querying is true, ascertaining as to whether a clock reset flag has been set; if the querying is false then storing the physiological measurement linked to a record of a current temporal parameter of the clock otherwise if the querying is true then storing the physiological measurement with both a delta time flag and a current temporal parameter of the clock; verifying whether a clock reset flag is set and if the clock reset flag is not set, displaying clock time on the display of the meter otherwise if the clock reset flag is set, prohibiting a display of the clock time on the display of the meter.

Other variations in the method are possible. For example, the method may further include establishing whether the meter is in communication with another or remote processor that has its own clock and if the meter is in communication with the another processor, checking if the clock reset flag is set; and if the checking returns a true then calculating a differential time between the local time clock of the remote processor and the clock of the meter and linking all stored analyte records with a differential time flag using the differential time from the calculating step, otherwise if the checking returns a false then checking to see if a temporal adjustment between the clock of the meter and the remote processor is needed. Alternatively, the determining step comprises checking for at least one internal error of the clock circuit or any circuitry of the meter; the determining step comprises checking for electrostatic discharge in the clock circuit, interruption in clock oscillation, or any fault or interruption in the circuitry of the meter; the displaying comprises a display of at least one recent physiological measurement; the prohibiting comprises a display of at least one recent physiological measurement. In the method, the temporal parameters comprise date and year; the analyte measurement may include a glucose measurement in a physiological fluid of the user.

In the aforementioned aspects of the disclosure, the steps disclosed may be performed by an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

Applicant's invention has achieved the goal of allowing persons with chronic diseases to use a very simple meter (i.e., one without any user input interface such as buttons, touch screen or voice recognition interface) with virtually none of its disadvantages when it comes to keeping track of physiological measurements for prospective or retrospective analysis of the physiological measurements. Therefore, the following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1:
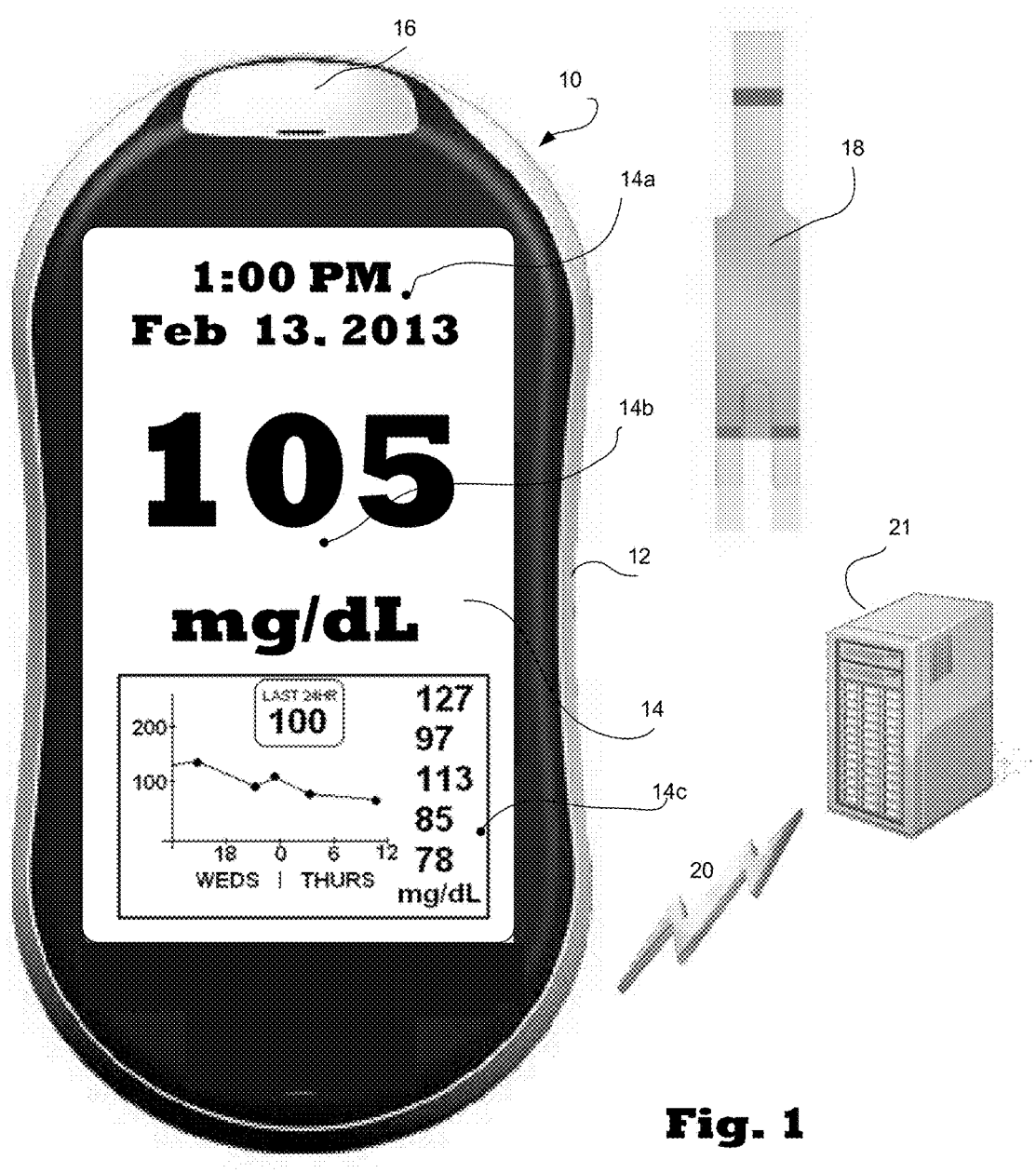
FIG. 1 illustrates a preferred blood glucose measurement system with a physiological meter and an analyte biosensor in the form of a disposable test strip.

FIG. 1 illustrates a diabetes management system that includes a meter 10 and a biosensor in the form of a glucose test strip 18. Note that the meter 10 may be referred to as a physiological measurement and management unit, a glucose meter, a meter, and a physiological measurement device. In an embodiment, the meter unit may be combined with an insulin delivery device, an additional analyte testing device, and a drug delivery device. The meter unit may be connected to a remote computer or remote server 21 via a cable (not shown) or a suitable wireless technology 20 such as, for example, GSM, CDMA, BlueTooth, WiFi and the like.

Referring back to FIG. 1, analyte measurement meter or meter unit 10 may include a housing 12 a display 14, and a strip port opening 16. The display 12 can be configured to show the temporal parameters 14a, physiological measurement 14b and past recorded physiological measurements that can be presented statistically in graphical form. The electronic components of meter 10 may be disposed on a circuit board 34 that is within housing 12. Although the meter 10 is shown as a blood glucose meter, other types of physiological meters can also utilize this technique devised by applicants. For example, the meter can be in the form a blood pressure monitor and the physiological measurements can be blood pressure taken during different times of the day; the meter can be in the form of a pulse oximetry meter with oxygen saturation values being the physiological measurements measured at various times of the day. Alternatively, the meter may include more than one physiological monitor. It should be clear that the technique devised by applicants here are not limited to the few examples described herein.

Figure 2:
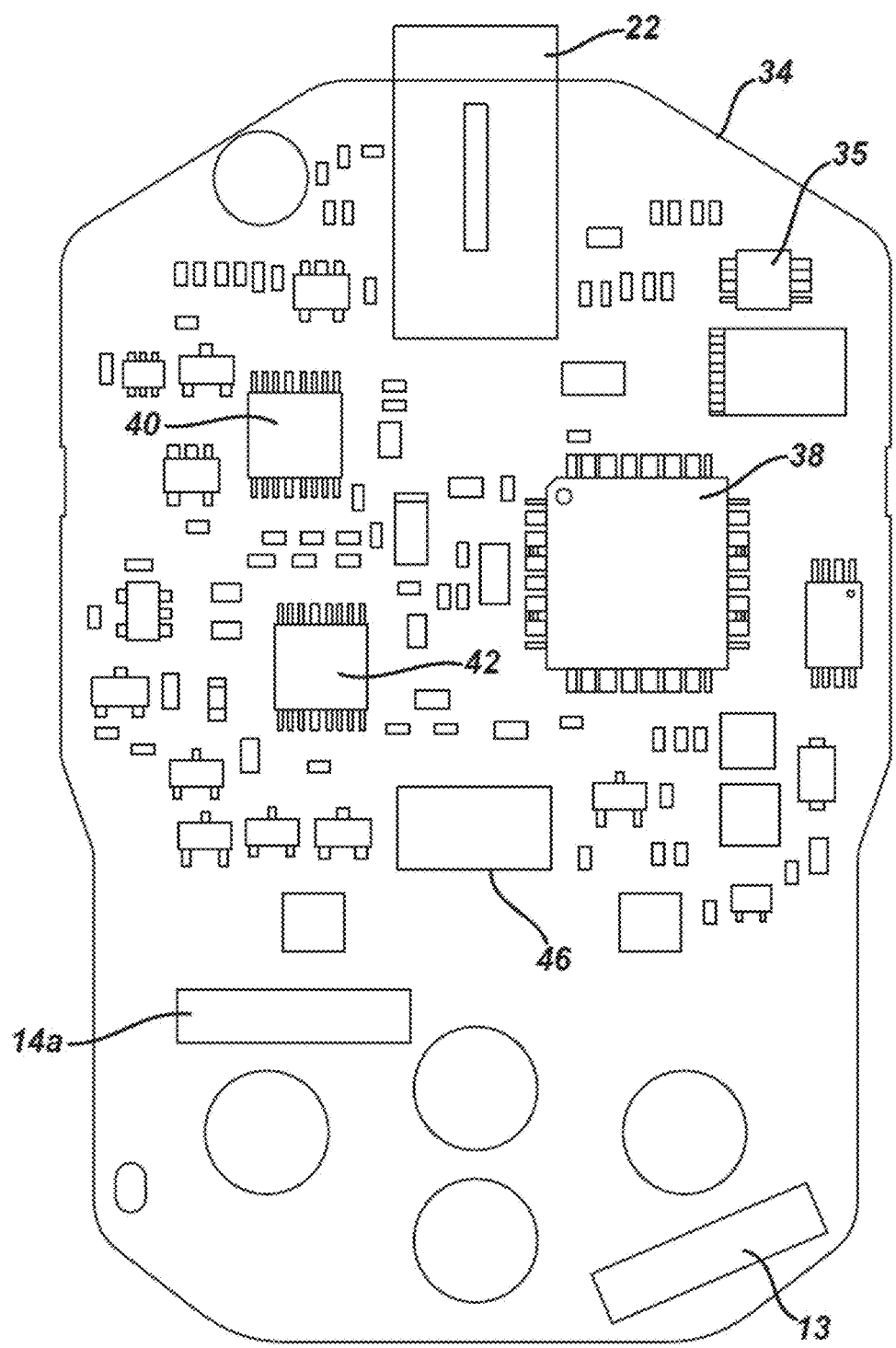
FIG. 2 illustrates the various components disposed in the meter of FIG. 1.

FIG. 2 illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock circuit 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, and data port 13.

Operational amplifier circuit 35 may include two or more operational amplifiers configured to provide a portion of the potentiostat function and the current measurement function. The potentiostat function may refer to the application of a test voltage between at least two electrodes of a test strip 18. The current function may refer to the measurement of a test current resulting from the applied test voltage. The current measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14a may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured to keep current temporal parameter related to the geographic region in which the user is located and also for measuring time. The meter unit may be configured to be electrically connected to a power supply such as, for example, a battery.

Strip 18 includes a reagent layer (typically glucose dehydrogenase (GDH) based on the PQQ co-factor and ferricyanide). In another embodiment, the reagent or enzyme may be replaced with the enzyme GDH based on the FAD co-factor. When blood or control solution is dosed into a sample reaction chamber of strip 18, glucose is oxidized by $GDH_{(ox)}$ and in the process converts $GDH_{(ox)}$ to $GDH_{(red)}$, as shown in the chemical transformation T.1 below. Note that $GDH_{(ox)}$ refers to the oxidized state of GDH, and $GDH_{(red)}$ refers to the reduced state of GDH.

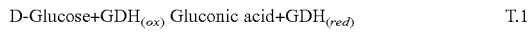

$$D\text{-Glucose}+GDH_{(ox)} \text{ Gluconic acid}+GDH_{(red)} \quad\quad T.1$$

Next, $GDH_{(red)}$ is regenerated back to its active oxidized state by ferricyanide (i.e. oxidized mediator or $Fe(CN)_6^{3-}$) as shown in chemical transformation T.2 below. In the process of regenerating $GDH_{(ox)}$, ferrocyanide (i.e. reduced mediator or $Fe(CN)_6^{4-}$) is generated from the reaction as shown in T.2:

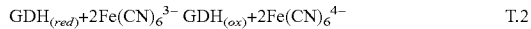

$$GDH_{(red)}+2Fe(CN)_6^{3-} \; GDH_{(ox)}+2Fe(CN)_6^{4-} \quad\quad T.2$$

Meter 10 may include electronic circuitry that can be used to apply a plurality of voltages to the test strip 18 and to measure a current transient output resulting from an electrochemical reaction in a test chamber of the test strip 18. The signal processor 38 of meter 10 is provided with a set of instructions for the method of determining an analyte concentration in a fluid sample.

As is known, the user inserts the test strip into a strip port connector of the test meter to connect at least two electrodes of the test strip to a strip measurement circuit. This turns on the meter 10 and the meter may recognize that the strip 18 has been inserted, the test meter 10 initiates a fluid detection mode. Once it has been determined that sufficient fluid amount has been deposited, the meter automatically initiate the glucose test. Details of this technique to determine sufficient volume for electrochemical testing are shown and described in U.S. Pat. Nos. 7,195,704; 6,872,298; 6,856,125; and 6,797,150, which documents are incorporated by reference as if fully set forth herein. A determination of the glucose concentration from the current transient output from the test strip 18 can be found in U.S. Pat. No. 7,749,371, patented Jul. 6, 2010, which was filed on 30 Sep. 2005 and entitled "Method and Apparatus for Rapid Electrochemical Analysis," which is hereby incorporated by reference in its entirety into this application.

Figure 3:
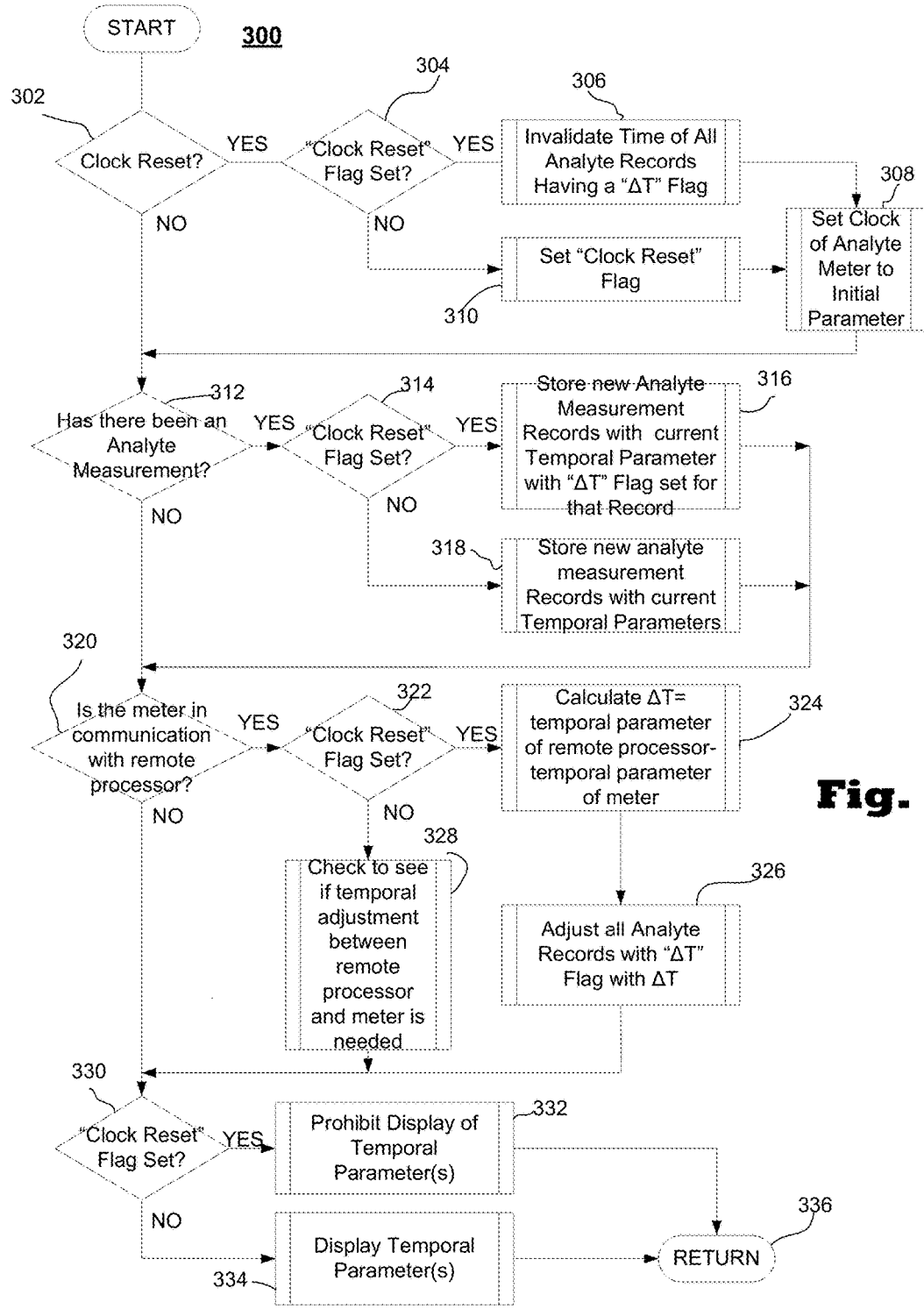
FIG. 3 illustrates the logic to allow for time record linkage to the physiological measurement record.

Referring to FIG. 3, applicant has devised a logical process 300 to allow for any physiological meter without a user input interface to utilize temporal parameters linked to physiological measurements and storing both the temporal parameters with the respective physiological measurements. Process 300 can be initiated whenever the meter is turned on, after a test measurement, or when connected to a remote processor, such as, for example, a personal computer, a smartphone, or a remote server 21. At step 302, a check is made by the microcontroller 38 whether at least one of a command to reset clock 42 or an occurrence of the clock 42 being reset has been made due to an error, command or application of power (e.g., such as during the insertion of a new battery). If step 302 returns a true, then microcontroller 38 evaluates as to whether a clock reset flag has been set at step 304. In the event the evaluating step 304 is false (or returning a "no"), then the controller 38 sets a "clock reset" flag as part of its program at step 310 and the clock 42 to its initial factory parameters at step 308. Otherwise if the evaluating step 304 is true then the system disqualify, at step 306 any physiological measurement record having a delta-time flag associated with the analyte record. Thereafter, the clock 42 is set to its initial parameters. The initial parameters may include the temporal parameters provided to the system during manufacturing of the meter. This may include the initial date and time programmed into any non-erasable memory of the clock circuit. As used herein, the phrase "disqualify" and variations on this root term means that the disqualified physiological measurement records cannot be used or shown to the user even though such records are available for purpose of diagnostics.

If the determining step 302 is false then the system query as to whether a physiological measurement has been made at step 312. If the querying is true, then the system ascertains, at step 314, as to whether a clock reset flag has been set. At step 314, if the querying is false then the system stores the physiological measurement linked to a record of a current temporal parameter of the clock at step 318, otherwise if the querying at step 314 is true then storing the physiological measurement with both a delta time flag and a current temporal parameter of the clock at step 316; verifying whether a clock reset flag is set and if the clock reset flag is not set, displaying clock time on the display of the meter otherwise if the clock reset flag is set, prohibiting a display of the clock time on the display of the meter when the physiological measurement record is reviewed. Applicants note that where meter utilizes an audible annunciator (with or without the display), the annunciator is also prohibited from annunciating the temporal parameters for the physiological measurement records. As used herein, the phrase "current temporal parameter" of the clock is intended to include at least a current time and preferably, current time, date and year.

If the query at step 312 returns a false then the system establishes at step 320 whether the meter is communication or preparing to communicate with a remote processor 21. If step 320 returns a true then the system checks to see if a "clock reset" flag has been set at step 322. If step 322 is true, a calculation is made at step 324 of ΔT where ΔT is a representation of a difference between the temporal parameter of the remote processor 21 versus the temporal parameter of the clock 42 of the meter. The symbol delta signifies that time stamp linked to the measurement record from one measurement to another correct relatively but not absolutely. Where the temporal parameter is in the form of hours or minutes (or even seconds), ΔT is a time differential between the remote processor 21 and the clock 42. Alternatively, where the temporal parameter is in the form of days, ΔT is a date differential between the remote processor 21 and the clock 42. Thereafter, at step 326, all stored physiological measurement records with the ΔT flag is adjusted with the calculated ΔT. For example, if the clock 42 is 2 hours faster than the remote processor clock then all records with the ΔT flag is subtracted by two hours; if the clock 42 is 4 hours slower than the remote processor clock then 4 hours are added to all records with the ΔT flag.

On the other hand, if the check in step 322 returns a false, meaning that the clock reset flag is not set then a check is made at step 328 to determine if a temporal adjustment is needed for the clock 42 based on the temporal parameters of the remote processor clock. For example, at step 328, if it is determined that the clock 42 is too fast, too slow or in a different time zone then a flag can be set or the clock 42 can be adjusted to have the same temporal parameters (e.g., time and date) as remote processor clock. This step 328 is intended to account for time drift or different time zones.

If step 320 cannot establish that the meter is in communication with the remote processor 21, verification is made at step 330 to determine if the clock reset flag was set. If step 330 returns a true, meaning that the clock reset flag was set, the system prohibits the meter from showing the temporal parameters (e.g., time or date) at step 332. If step 330 returns a false, meaning that there is no clock reset flag established, then the meter is allowed to display the temporal parameters at step 334. Both steps 332 and 334 revert to the main routine at step 336.

In the logic devised by applicant, the determining step 302 may include checking for at least one internal error of the clock circuit or an error in any circuitry of the meter or the processor. Such error may include electrostatic discharge in the clock circuit or any circuitry of the meter or the meter circuit. It is noted that the displaying of the temporal parameters may include a display of at least one recent physiological measurement. Alternatively, the prohibition of the temporal parameters may include prohibiting a display of at least one recent physiological measurement or in other words, prohibiting the display of temporal parameters when the physiological measurement value is displayed or annunciated. In the method, the temporal parameters comprise date and year. Additionally, the method described herein can be programmed into any suitable processor so that the steps of the method can be carried out by such processor.

Applicant notes that this heretofore new technique is also applicable to any physiological measurement of physiological parameters and is not limited to analyte (e.g., glucose) measurement of blood. Moreover, the technique has advanced the state-of-the art by allowing for the technical effects of a very simple meter (i.e., one without any user input interface) with virtually none of its disadvantages when it comes to keeping track of physiological measurements for prospective or retrospective analysis of the measurements.

Accordingly, while the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of operating a buttonless physiological measurement system, including temporal adjustment of the system from a remote clock, the system having a physiological meter with a microprocessor linked to a clock, memory, and display, in which the meter does not include a user input interface to permit a user to set temporal parameters, including time, for the physiological meter, and in which the clock of the meter is operable in one of relative time mode in which a relative delta-time flag is stored with measurements or an absolute time mode in which a relative delta-time flag is not stored with measurements, the method comprising the steps of:

following an initiating event of the physiological meter, and automatically using the microprocessor, operating the clock of the meter in the relative time mode;

responsive to a first physiological measurement being made by the meter with the clock operating in the absolute time mode, storing into memory of the microprocessor a first physiological measurement record comprising the first physiological measurement and a first temporal parameter of the clock;

responsive to a second physiological measurement being made by the meter with the clock operating in the relative time mode, storing into the memory of the microprocessor a second physiological measurement record comprising the second physiological measurement, the relative delta-time flag and a second temporal parameter of the clock;

preventing the meter from displaying any physiological measurement record having the relative delta-time flag;

responsive to communication with a remote processor having a remote clock:

receiving temporal parameters from the remote clock and calculating a differential between the received temporal parameters and the temporal parameters of the clock of the meter;

setting the temporal parameters of the clock of the meter to the received temporal parameters and operating the clock of the meter in the absolute time mode; and removing the relative delta-time flag from the second physiological measurement record and adjusting the second temporal parameter to be an absolute temporal parameter using the calculated differential;

responsive to the clock of the meter operating in the absolute time mode, displaying the first physiological measurement record including the first temporal parameter and the second physiological measurement record including the adjusted second temporal parameter;

responsive to the clock of the meter operating in the absolute time mode, enabling clock time to be displayed on the display of the meter when the physiological measurement record is being reviewed; and responsive to the clock operating in the relative time mode, prohibiting a display of the clock time on the display of the meter when the physiological measurement record is being reviewed.

2. The method of claim 1, further comprising:

establishing whether the meter is in communication with another or remote processor that has its own local absolute time clock;

responsive to the meter being in communication with the another processor, calculating using the microprocessor, a differential time between the local time clock of the remote processor and the linked clock of the meter;

linking all stored measurement records having a relative delta time flag by determining a corresponding absolute temporal parameter using the differential time from the calculating step; and determining, using the microprocessor, whether a temporal adjustment between the linked clock of the meter and the clock of the remote processor is needed and then applying the temporal adjustment to the clock of the meter.

3. The method of claim 1, in which the initial determining step comprises checking for at least one internal error of the clock circuit or any circuitry of the meter.

4. The method of claim 1, in which the initial determining step comprises checking for electrostatic discharge in the clock circuit or any circuitry of the meter.

5. The method of claim 1, in which the displaying comprises a display of at least one recent physiological measurement.

6. The method of claim 1, in which the prohibiting comprises a display of at least one recent physiological measurement.

7. The method of claim 1, in which the temporal parameters comprise date and year.

8. The method of claim 1, in which the physiological measurement comprises an analyte measurement.

9. The method of claim 8, in which the analyte measurement comprises a glucose measurement in a physiological fluid of the user.

10. A physiological meter with temporal adjustment from a remote clock, the meter comprising:
   a clock operable in one of relative time mode in which a relative delta-time flag is stored with measurements or an absolute time mode in which a relative delta-time flag is not stored with measurements, wherein the meter does not include a user input interface to permit a user to set temporal parameters, including time, of the clock; and
   a microprocessor linked to the clock, a memory, and a display, and configured to perform a method, the method comprising the steps of:
      following an initiating event of the physiological meter, and automatically using the microprocessor, operating the clock of the meter in the relative time mode;
      responsive to a first physiological measurement being made by the meter with the clock operating in the absolute time mode, storing into memory of the microprocessor a first physiological measurement record comprising the first physiological measurement and a first temporal parameter of the clock;
      responsive to a second physiological measurement being made by the meter with the clock operating in the relative time mode, storing into the memory of the microprocessor a second physiological measurement record comprising the second physiological measurement, the relative delta-time flag and a second temporal parameter of the clock;
      preventing the meter from displaying any physiological measurement record having the relative delta-time flag;
      responsive to communication with a remote processor having a remote clock
         receiving temporal parameters from the remote clock and calculating a differential between the received temporal parameters and the temporal parameters of the clock of the meter,
         setting the temporal parameters of the clock of the meter to the received temporal parameters and operating the clock of the meter in the absolute time mode, and
         removing the relative delta-time flag from the second physiological measurement record and adjusting the second temporal parameter to be an absolute temporal parameter using the calculated differential;
      responsive to the clock of the meter operating in the absolute time mode, displaying the first physiological measurement record including the first temporal parameter and the second physiological measurement record including the adjusted second temporal parameter;
      responsive to the clock of the meter operating in the absolute time mode, enabling clock time to be displayed on the display of the meter when the physiological measurement record is being reviewed; and
      responsive to the clock operating in the relative time mode, prohibiting a display of the clock time on the display of the meter when the physiological measurement record is being reviewed.

* * * * *